United States Patent [19]
Zelin

[11] Patent Number: 5,821,399
[45] Date of Patent: Oct. 13, 1998

[54] AUTOMATIC TEST PARAMETERS COMPENSATION OF A REAL TIME FLUID ANALYSIS SENSING DEVICE

[75] Inventor: Michael P. Zelin, Brooklyn, N.Y.

[73] Assignee: I-Stat Corporation, Princeton, N.J.

[21] Appl. No.: 656,276

[22] PCT Filed: Jul. 16, 1993

[86] PCT No.: PCT/US93/06736

§ 371 Date: Jan. 16, 1996

§ 102(e) Date: Jan. 16, 1996

[87] PCT Pub. No.: WO95/02827

PCT Pub. Date: Jan. 26, 1995

[51] Int. Cl.⁶ ........................... G01P 5/00
[52] U.S. Cl. ............ 73/1.02; 204/403; 324/439; 422/61
[58] Field of Search ............ 73/1.02, 1.03, 73/64.53; 204/400, 403, 409; 324/439; 422/61, 63, 82, 82.02; 436/8, 43, 808

[56] References Cited

U.S. PATENT DOCUMENTS

| | | | |
|---|---|---|---|
| 4,301,412 | 11/1981 | Hill et al. | 324/442 |
| 4,301,414 | 11/1981 | Hill et al. | 324/446 |
| 4,654,127 | 3/1987 | Baker et al. | 204/409 X |
| 5,022,980 | 6/1991 | Tanaka et al. | 73/1.02 X |
| 5,096,669 | 3/1992 | Lauks et al. | 324/439 X |
| 5,112,455 | 5/1992 | Cozzette et al. | 204/400 X |
| 5,204,264 | 4/1993 | Kaminer | 73/102 X |

FOREIGN PATENT DOCUMENTS

| | | |
|---|---|---|
| 03-181861 | 7/1991 | Japan . |
| 03-181862 | 7/1997 | Japan . |

*Primary Examiner*—Hezron E. Williams
*Assistant Examiner*—Daniel S. Larkin
*Attorney, Agent, or Firm*—Pennie & Edmonds LLP

[57] ABSTRACT

A method for automatic fluid flow compensation in disposable fluid analysis sensing devices is disclosed. The method is designed to keep the test conditions from sample to sample substantially unchanged. This is accomplished by using information about the preceding and/or current test measurements to automatically offset parameter variations of the disposable devices and the reading apparatus caused by manufacturing tolerances, wear of the mechanical parts, fluid viscosity differences and others. At each consecutive test measurement the method uses a compensation of the position of the actuating element to offset the difference between the previous test measurement and a factory prespecified value. The method and system result, over the lifetime of the instrument, in a substantially unchanged flow of the analyzed fluid and reduction of the influence of a variety of external factors on the test measurements.

20 Claims, 15 Drawing Sheets

AUTOMATIC TEST PARAMETERS COMPENSATION OF A REAL TIME FLUID ANALYSIS SENSING DEVICE

FIELD OF INVENTION

The present invention relates to a method and system for compensation of test parameter variations. In particular, the invention relates to a method and system for compensating the fluid flow deviations due to wear and other factors influencing the performance of a real time fluid analysis test system.

BACKGROUND OF THE INVENTION

The testing of blood or other body fluids for medical evaluation and diagnosis has traditionally been performed in large, well equipped centralized laboratories. Such laboratories offer a wide range of efficient and accurate testing procedures for a high number of fluid samples. Centralized processing of fluid test samples has important advantages including the use of sophisticated, automated analytical technology and highly trained personnel capable of calibrating and actively controlling operating parameters of this technology. However, the centralized type of testing has a number of disadvantages as well. An important one, for example, is that the test results are typically not immediately available to the physician who requested the test. Delays reaching several days are often caused by the fact that each sample has to be collected, transported to the centralized laboratory and then processed. The analysis results can only then be communicated to the physicians, so that even in a hospital setting there may be significant delays, jeopardizing on occasions the patient's health. In addition, test instruments designed for processing large numbers of samples, require specialized maintenance, especially for elements of the system in contact with the fluid, such as sensors and flow paths. Therefore, there is a recognized need for testing apparatuses which would permit the physician to obtain immediate results while examining a patient, whether in his office, in the hospital emergency room, or at the patient's bedside elsewhere in a hospital.

A number of prior art testing systems have been designed to meet such need. Many devices are only capable of making simple test measurements. For example, well known are glucose meters, based on the use of calorimetric strips which require the tested fluid to be directly applied to a sensing region. Other test systems, such as the Biotrack PT analyzer made by the Ciba Corning Diagnostics Corp. rely on passive capillary draw within a cartridge to move the test fluid to the sensing region. A similar approach is used in systems such as the Kyoto Daiichi glucose sensor, the U.S. Surgical Corporation's Statcrit hematocrit sensor system and the Hemocue glucose and hematocrit cartridges made by Mallinkrodt Sensor Systems, Inc. In a different approach, the TAS instrument made by Cardiovascular Diagnostics generates an oscillating magnetic field which causes magnetic particles to dissolve and mix a fluid contained within the cartridge. In all these products, the test system is adapted for relatively simple measurements with no instrument control over the actions of fluids within the cartridges.

Other prior art fluid analysis systems can perform more complex measurements and have a correspondingly more complicated design. Several systems of this type (notably the Abbott Vision system and the EPOC test system developed by Abaxis) use centrifugal forces created by high-speed rotation of a cartridge containing the test sample to separate out its major components, and an optical analysis instrument which relies on optical transmission differences to make the measurement. This design approach is, however, not suitable for bedside analysis due to the large size of the instrument.

In order to avoid the problem of specialized maintenance of portions of the test equipment which are in direct contact with the test samples, several prior art sensing instruments utilize disposable test measurement cartridges. For example, the test system disclosed in U.S. Pat. Nos. 4,301,412 and 4,301,414 to Hill et al. employs a disposable sample card carrying a capillary tube and two electrodes. The sample card is inserted into an instrument to read the electrical potential generated at the electrodes. While simple conductivity measurements can be made with this system, there is no provision for the full range of tests which are generally desirable. Similarly, the device disclosed in U.S. Pat. No. 4,756,884 to Hillman et al. only provides limited testing capabilities with a transparent plastic capillary flow card which permits external optical detection of the presence of an analyte.

Other prior art devices of more general utility suffer the disadvantage that excessive manual intervention is necessary in the testing process. For example, U.S. Pat. No. 4,654,127 to Baker et al., shows a single-use sensing device having a species-selective sensor in a test chamber. The operator must manually fill a sample chamber with the test sample, input data to a reading instrument, and respond to prompts from the instrument. Then, the device is manually inserted into the reading instrument. When prompted by the instrument, a further manual rotation of the reservoir releases the sample to the sensors under the force of gravity. Although equipment of this type is capable of performing a useful range of tests, the high number of manual operations involved in interacting with an instrument produces a correspondingly high number of opportunities for an operator error in timing or technique, which may and often does have a detrimental impact on the reliability of the performed measurements.

Yet another solution is presented by the Biotrack 516 apparatus made by Ciba Corning Diagnostics Corp. for agglutination assays. The system is a portable analyzer based on a discardable cartridge which houses two glass vials filled with fluids. After the blood sample passes under the force of gravity into a chamber, the instrument sequentially breaks the vials, releasing fluid to dilute and prepare the sample for the measurement. While requiring relatively little experience from the operator, the system presents no possibility to automatically adjust test measurement parameters.

Thus, while in many cases presenting viable alternatives to the centralized processing testing, prior art products also share substantial shortcomings including a relatively narrow range of test capabilities, lack of control over the test parameters which control is critical for the consistency of the test results over time, and the frequent necessity of employing highly trained laboratory technicians to perform the measurements and maintain the equipment in order to assure their accuracy and reliability and enhance the usefulness of the obtained results.

In order to overcome such limitations a test control system for real time analysis must provide a portable, inexpensive way to make apparatus with a fool-proof operation adaptable for a wide variety of tests. For optimal cost effectiveness, such a real time system would require minimum skill to operate, while offering high testing speed, and consistent and reliably accurate test results. Ideally, a successful device would eliminate operator technique as a source of error by eliminating the need for manual intervention, while providing for automatic correction and self-adjustment of the test parameters.

U.S. Pat. Nos. 5,096,669 (the "'669 patent") and 5,112,455 (the "'455 patent"), assigned to the same assignee and hereby explicitly incorporated by reference describe a system for testing blood which can be used by a physician to obtain immediate results at the patients side. The system consists of a hand-held, battery operated instrument and unit cartridges each of which is used to measure a multiplicity of analytes on a single whole blood sample. An important advantage of this system is the fact that the process of using it requires minimum human intervention. This feature ensures that the result delivered to the physician can be relied upon with little concern as to the level of skill of the individual who has performed the test. The i-STAT system based on the disclosure of the '669 patent also eliminates the need for special maintenance of the sensors and the flow paths since these test components are parts of a disposable cartridge replaced after each measurement by a new one. Thus, the i-STAT product combines some of the best elements of centralized laboratory instrumentation and hand-held cartridge based systems.

Specifically, as described in the '669 patent, the instrument utilizes a disposable sensing device in which during the test two fluids are consecutively moved over an array of sensors to determine the concentration of substances in the test sample. The first fluid is used for calibration of the sensors and prior to use is housed in a sealed pouch on the cartridge. The second fluid is the actual test fluid sample, typically a blood sample.

In use, after the calibration of the sensor elements, the actual measurement is initiated by depressing an air bladder in the cartridge which forces air to move all fluids within the cartridge along the fluid paths. In the process, the calibration fluid is first forced out of the sensor area. Next, the air bubble separating it from the test sample passes over the sensors, and finally the blood sample is pushed over the sensors for a predetermined period of time to conduct the actual measurements.

The i-STAT system requires minimum physical intervention on the part of the operator and is very fast (test results from a variety of measurements are typically obtainable within about 2 minutes). In addition, the disposable i-STAT system cartridge is provided with a pair of electrodes that comprise a conductivity sensor which measures the electrical resistance of the fluids at each stage of the measurement process. This allows the instrument to monitor the test and, by comparing measurement data to factory preset thresholds, determine whether test parameters are deviating from the standard limits. (For instance this control can determine whether the operator has collected sufficient blood sample to conduct a proper test).

Despite the apparent advantages of the i-STAT system it will be recognized by those skilled in the art that the mechanical elements of its fluid flow control may wear over the lifetime of the instrument, or become misadjusted for various reasons, such as improper handling of the reader. Such variations can affect the amount of sample fluid which is delivered to the sensors. These variations can in turn lead to variations in the amount of "carryover" of calibrant into the sample (incomplete clearance of calibrant from the sensors by the sample). As the software instructions in the instrument include calibration factors designed to determine concentrations of elements in the test sample based upon a fixed nominal amount of carryover, these variations can ultimately lead to an increased variation in the concentrations of elements in the test sample reported by the instrument.

In order to keep the complexity of the system at a minimum and make it cost effective, the i-STAT device provides no means for the operator to adjust the mechanical system. Therefore, unless the instrument has the ability to adjust itself, it would have to be returned back to the factory if and when its fluid control system moves out of the specification boundaries. Although optical and mechanical sensing devices which would control the mechanical elements of the portable i-STAT system could be used these are not the best type of solutions due to the complexity and cost of the required precision, compact design.

Thus, it is perceived that notwithstanding the advantages of this system, a software based method is required to automatically compensate for various deviations which may occur during the life time of the instrument as a result of mechanical wear, and other potential sources of measurement error. Such compensation may be used to relax the requirements on the precision mechanical parts of the instrument, increase the accuracy and reliability of the measurements and prolong the useful life of the instrument.

SUMMARY OF THE INVENTION

Accordingly, it is an object of the present invention to provide a means for automatic correction of the operation of a fluid control system for real time fluid sensing systems employing disposable cartridges.

It is another object of the present invention to provide an automatic compensation method and a system capable of maintaining consistent performance over the life time of a fluid sensing instrument under conditions of mechanical wear or misalignment of the mechanical components within the instrument.

It is yet another object of the present invention to provide a software based method for the automatic compensation of the parameter misadjustments and a system to implement such method.

In accordance with the present invention the automatic compensation method and system are based on the characteristic signal seen at the output of a fluid conductivity sensor which is mounted on each disposable cartridge. The sensor output signal is proportional to the electrical resistance measured between a pair of conductivity electrodes and can be used to determine the time when a particular fluid is positioned between those electrodes. Specifically, the resistance of the calibration solution typically has a relatively low, constant value. As the calibrating fluid is being displaced by the air bubble separating it from the test sample, the resistance measured between the electrodes rises sharply, due to the dielectric properties of the air. Finally, in the last segment of the test process, the measured resistance drops back down to a level determined by the electrochemical properties of the blood sample.

The sharp differential between the electrical resistance properties of the two fluids and the air enables the control system of the present invention to accurately determine the time relationships between the motions of the moving parts of the mechanical system and the flow of fluids over the sensors. Thus, the time position relative to the beginning of the test when the electrical resistance measurement reaches a first specified value (referred next as the rise time), and falls below a second value (referred next as the fall time) can be used as an indication of the performance of the mechanized fluid control system against predetermined specifications.

In accordance with the present invention there are two approaches to keeping the test parameters substantially unchanged over a large set of test measurements.

In one preferred embodiment of the present invention the automatic compensation method is based entirely on measurements from the previous cartridges. In this method, the total fluid displacement time measured from the beginning of the fluid displacement is kept constant. Similarly, the speed of the actuating element is constant in all measurements and the compensation is accomplished by changing the initial position of the actuating element prior to the beginning of the fluid displacement. In operation, after each successful sensing, the system compares the rise time of the measured resistance curve to a preset factory threshold and marks the difference as being positive or negative. This difference is stored and used in the following measurement to correct the physical position of the actuating element. For example, if the rise time of the resistance curve is shorter than the factory preset value, the compensation method automatically adjusts the initial position of the actuating element to start the actual motion of the fluid somewhat later during the next fluid displacement operation.

Alternatively, if the measured rise time is longer than the preset factory value, the method compensates by adjusting the initial position of the actuating element so that for the next test cartridge the actual motion of the fluid will start earlier during the next fluid displacement operation. (Physically, the corrections correspond to positioning the actuating element of the reader higher or lower with respect to an air bladder in the cartridge described in the '669 patent, the depressing of which is used to initiate the fluid displacement during test measurements). The unit correction amplitude after each test is identical, its direction being determined by the sign of the difference between the resistance rise time during the previous measurement and the factory specified mean rise time value. The total correction amplitude which is added to the factory preset value, however, is modified each time by adding or subtracting one unit to the previous value. This mode of compensation ensures that it is targeted to respond to the relatively slow changes in the physical properties of the system associated with wear of mechanical components, without adding extra variability by responding to the relatively large sensing device to device variations in the fluid arrival times.

The first embodiment is preferred because it both maintains a constant length of time for the fluid displacement operation and therefore providing the maximum precision to the signal processing algorithms described in the '455 patent and maintains a constant speed of fluid displacement to maintain maximum precision in the degree of carryover.

In a second and third embodiments of the present invention the volume of the test fluid samples delivered to the sensors is kept constant over a set of measurements by using not only data from previous measurements but concurrent sensor output information from the sensing device as well. In accordance with these embodiments, both the speed of the actuation element and the fluid displacement time for test sample sensing may be varied during a test measurement. The goal in each case is to ensure a constant volume of the test fluid sample passing over the sensors.

In accordance with the second embodiment of the present invention, the target time for a standard test fluid sample to pass over the sensors is used. For a constant speed of the actuation element this time is proportional to the sample volume moved over the sensor elements, so that by keeping the fluid displacement time constant, the compensation method of the present invention effectively maintains a constant test sample volume. To this end, the instrument continuously monitors the output of the conductivity sensors. After the measured resistance reaches the second predetermined threshold (at the fall time of the resistance curve), indicating the time when the test sample is over the sensor elements, the actuation element is pressed for the target test time. In this embodiment, the motion speed of the actuation element is kept constant.

In a third embodiment of the present invention, a target volume of the test sample delivered to the sensors is maintained for each test by modifying the speed of the actuating element, keeping the fluid displacement time constant.

The preferred embodiments of the present invention only require the implementation of software based automatic compensation methods, which by reducing variations of fluid displacement parameters effectively increase the consistency and reliability of the output measurements made by each sensor of the sensing device of the fluid sensing system.

BRIEF DESCRIPTION OP THE DRAWINGS

These and other objectives, features and advantages of the present invention are described in following detailed description of the preferred embodiments and are illustrated in the accompanying figures in which.

FIGS. 5 A, 5B and 5C show the position of the fluids at three different points during the fluid displacement.

Figure 5A:
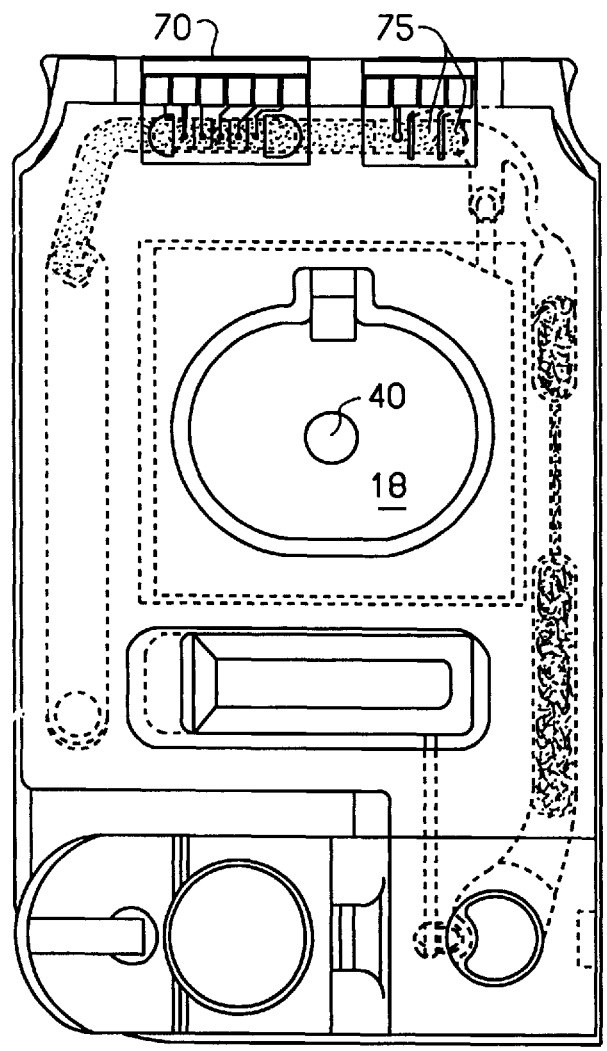

FIG. 5A shows the sample fluids at the beginning of the fluid displacement.

Figure 5B:
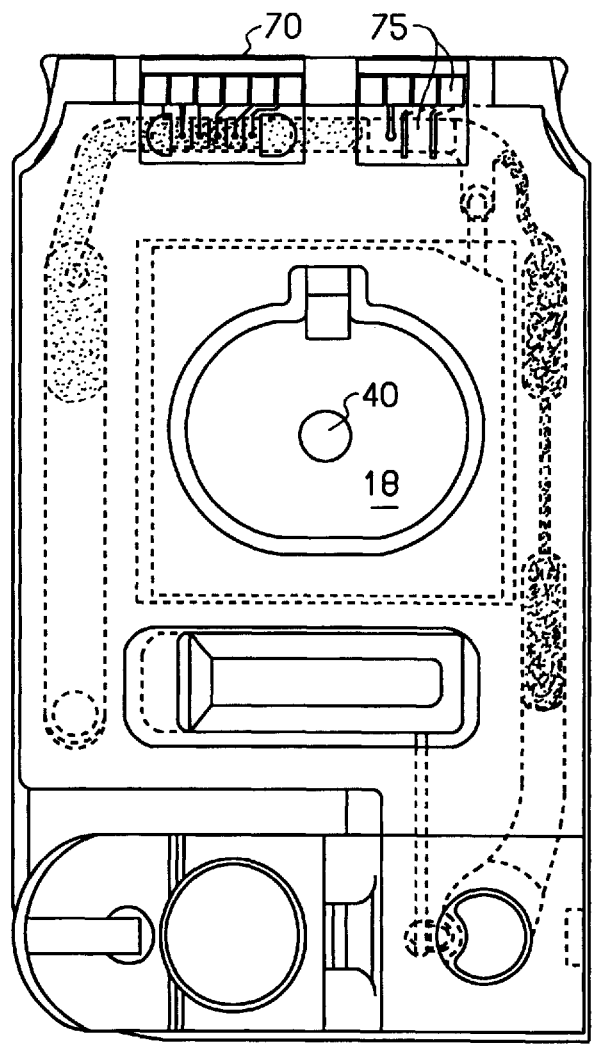

FIG. 5B shows the position of the fluid at a later point in time when the air segment is over the conductivity sensors.

Figure 5C:
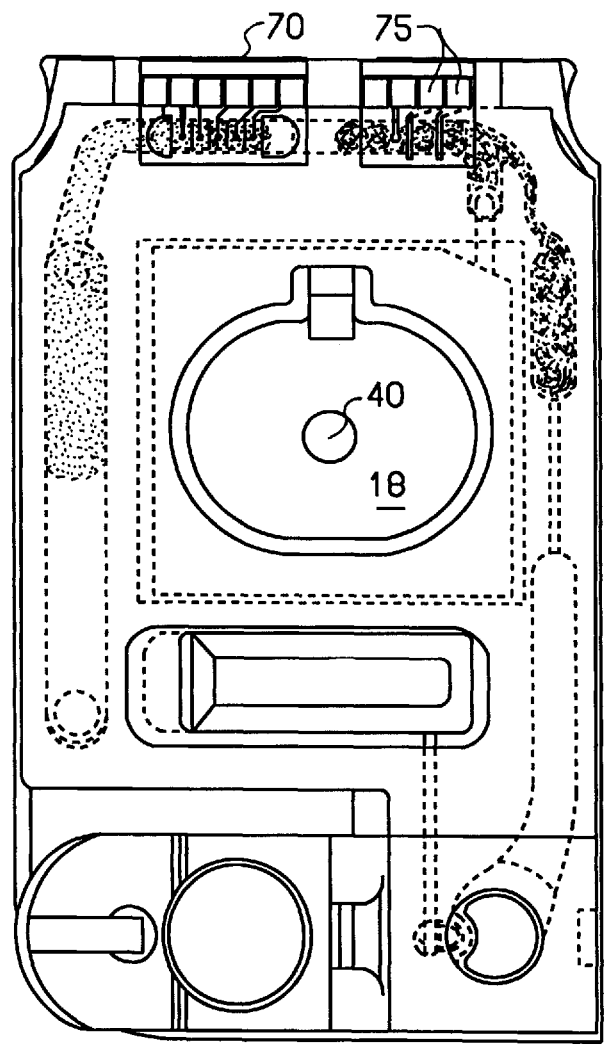

FIG. 5C shows the position of the fluid at the end of the test when the sample fluid has been displaced over the sensor array.

Figure 6:
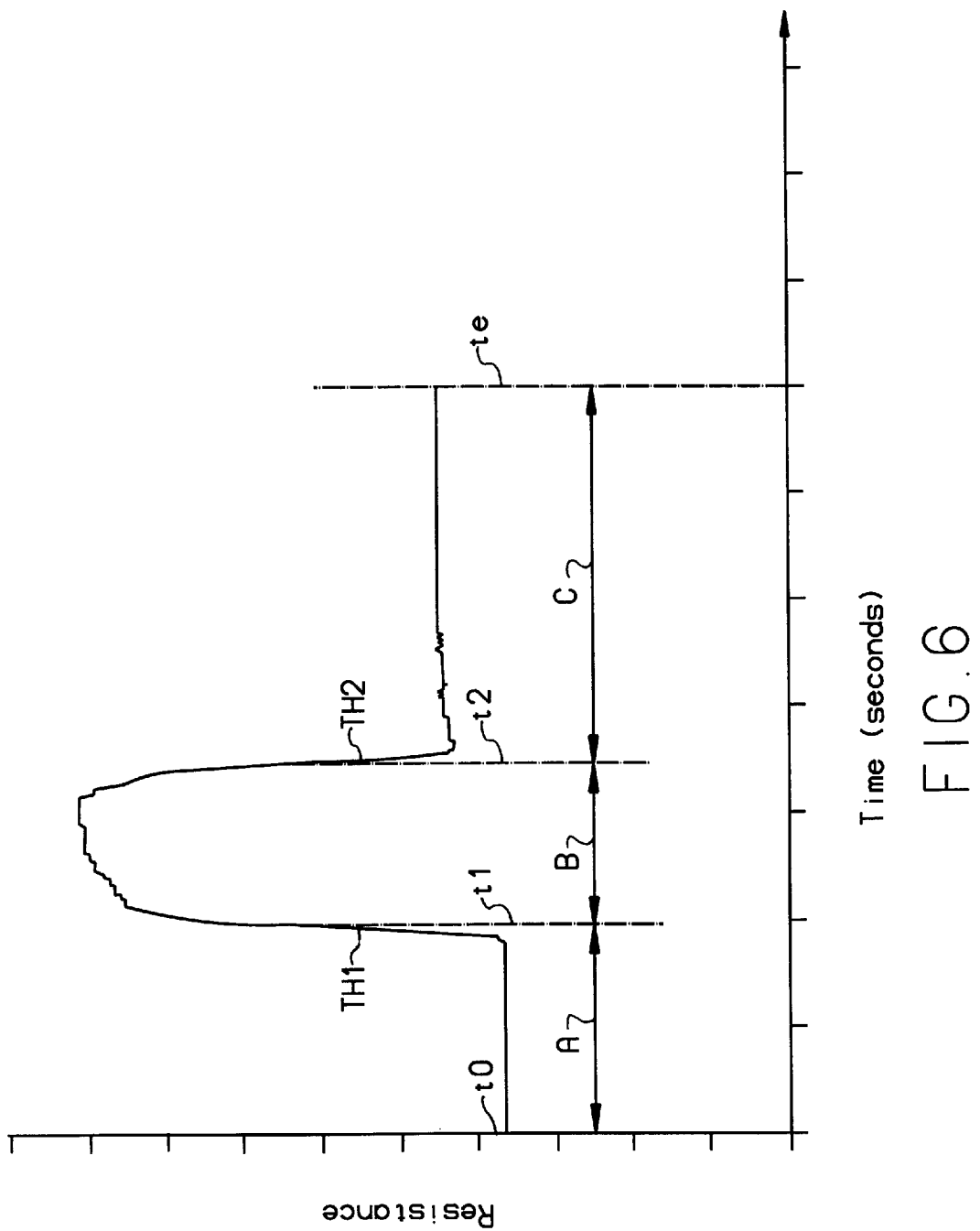

FIG. 6 illustrates a typical resistance signal obtained from the conductivity sensor during the test measurement.

Figure 7A:
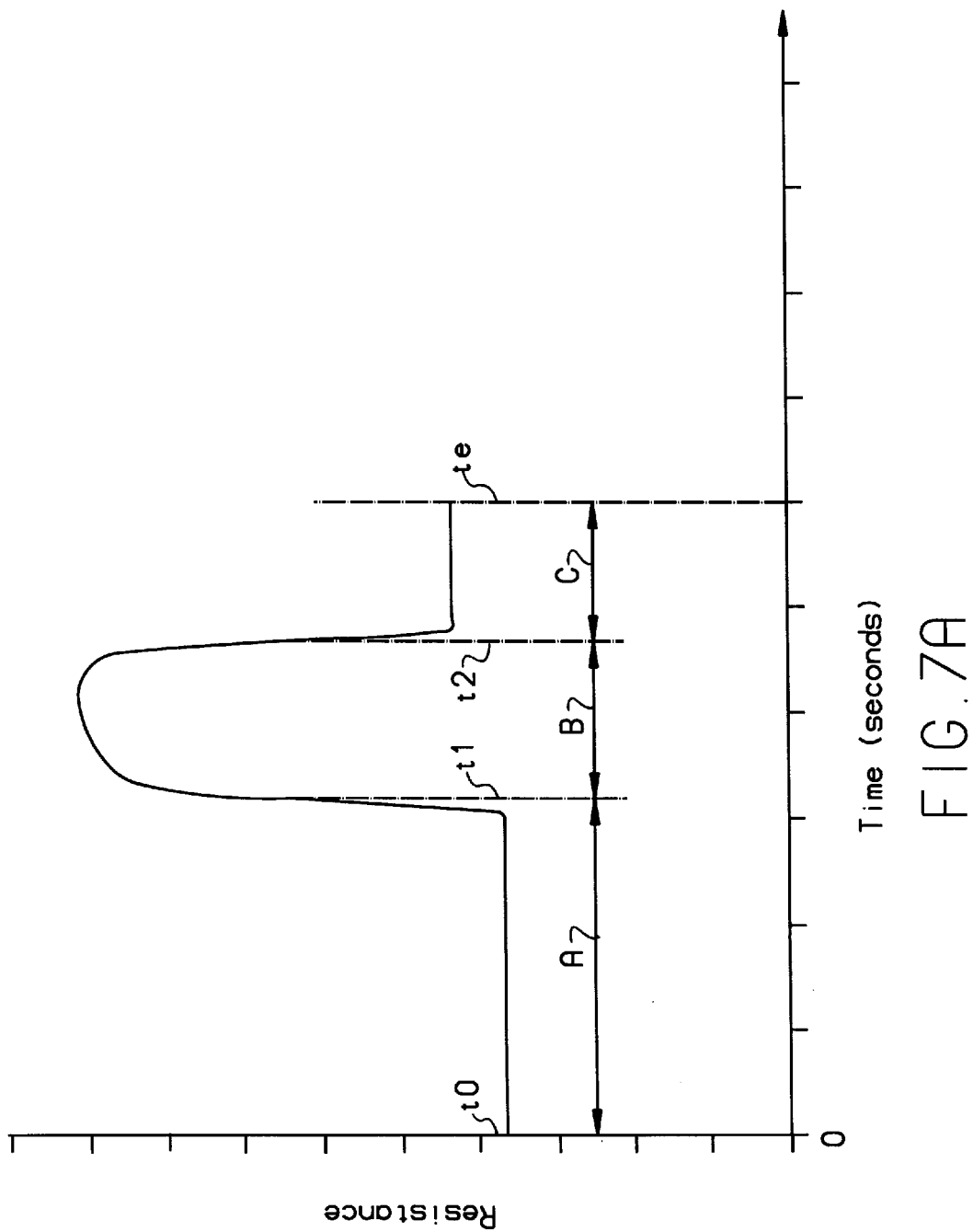
Figure 7B:
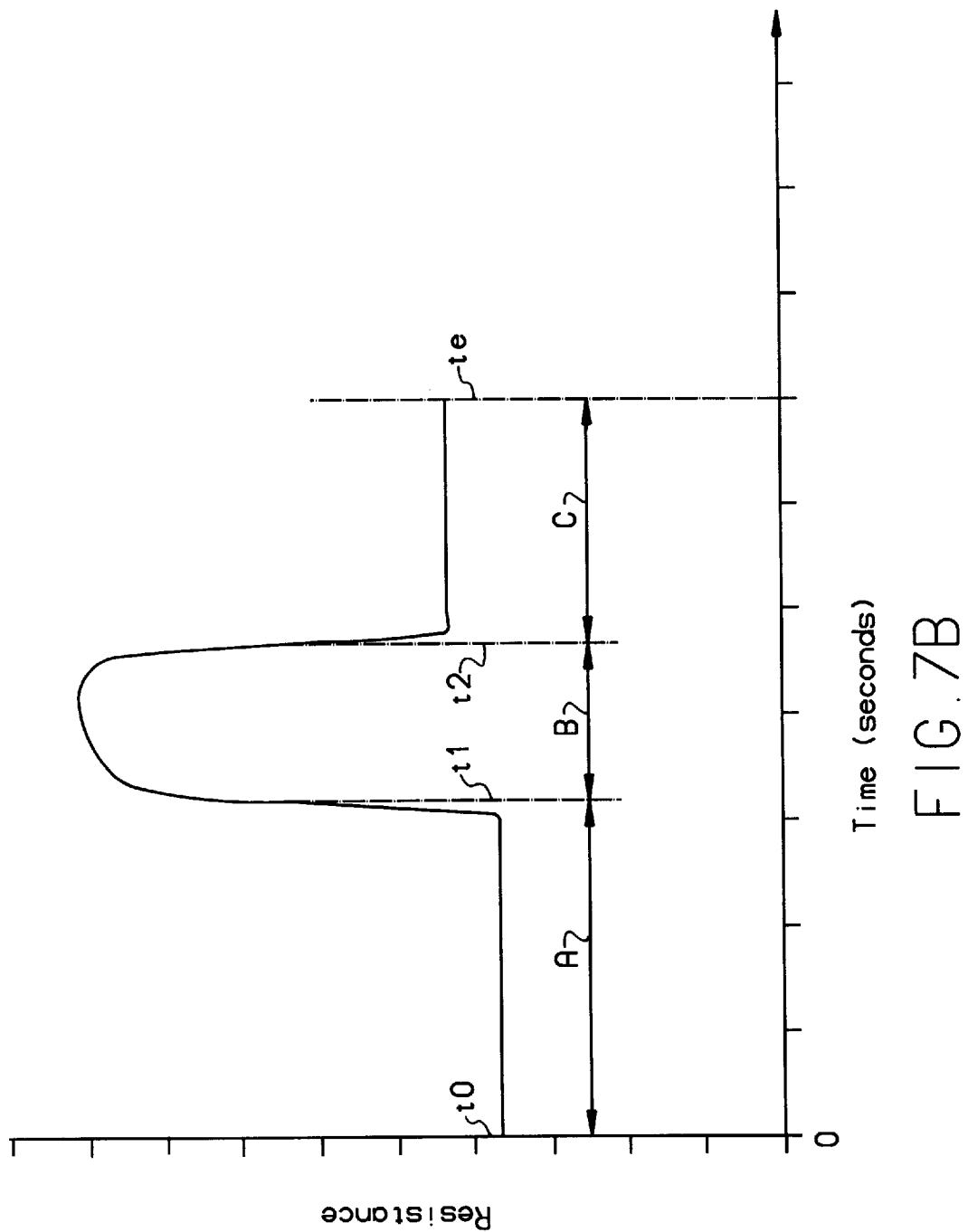
Figure 7C:
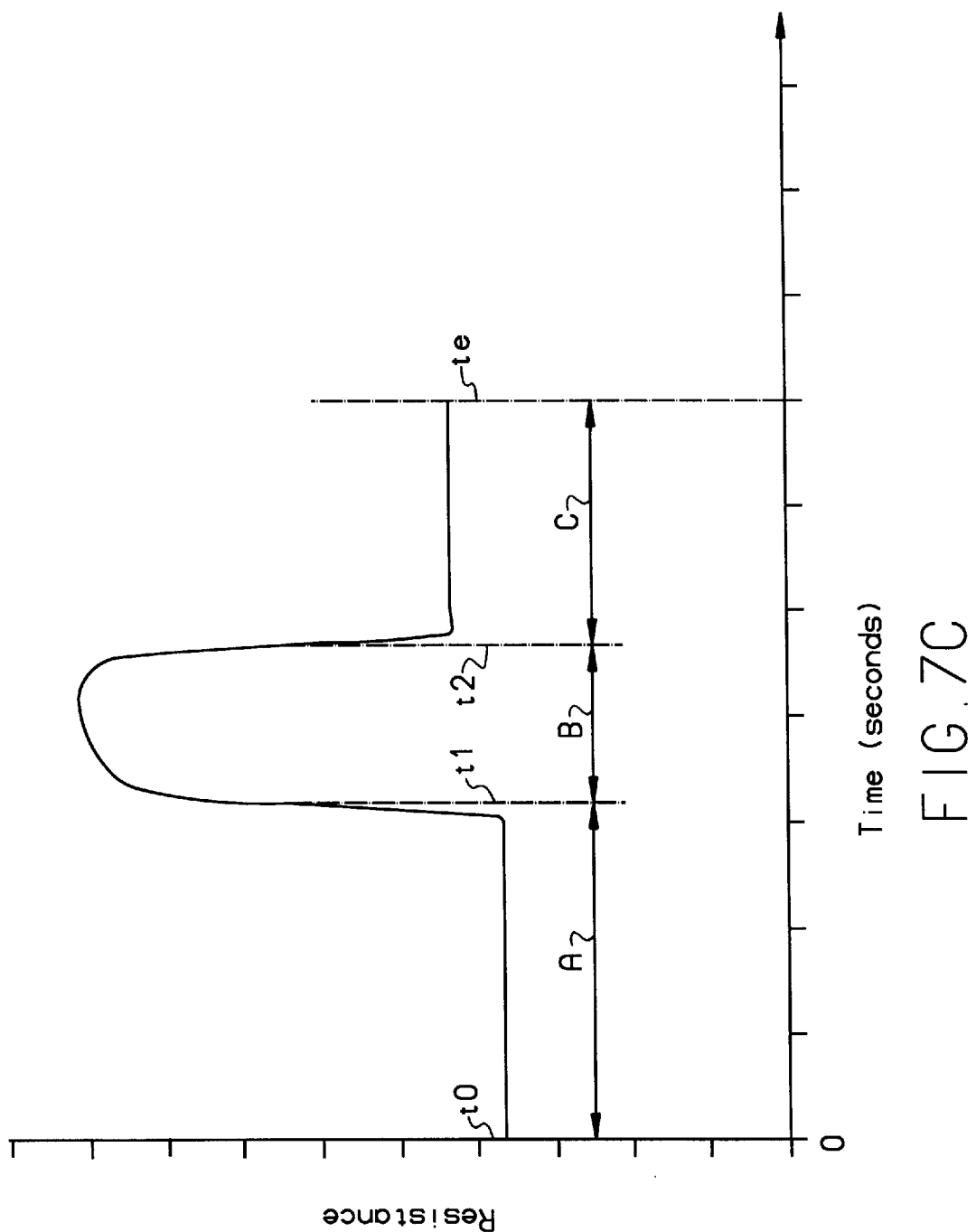

FIG. 7A, 7B and 7C illustrate possible variations of the resistance signal due to mechanical wear and other factors influencing the test measurements.

Figure 8:
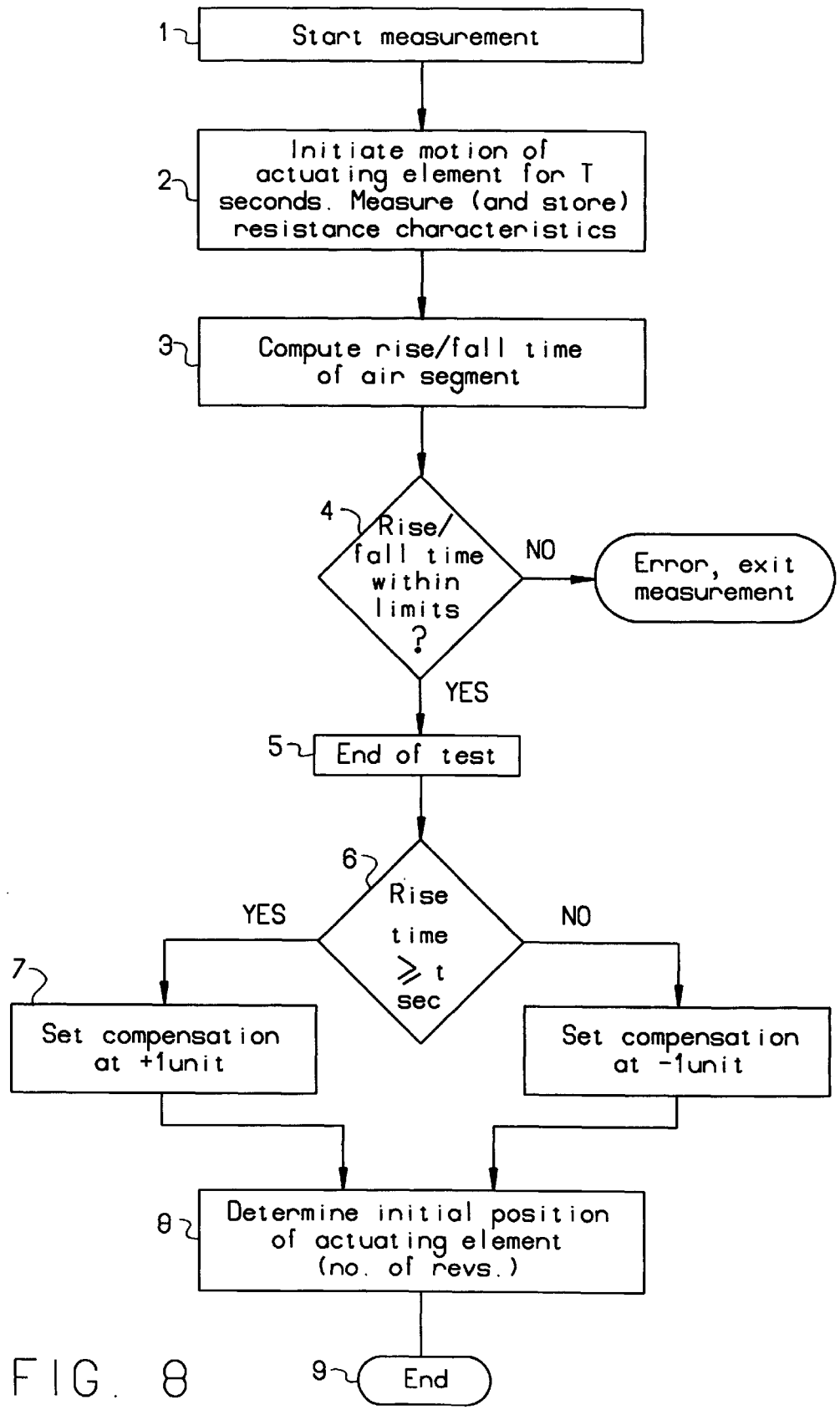

FIG. 8 is a block diagram of a preferred embodiment of the automatic compensation method of the present invention.

Figure 9A:
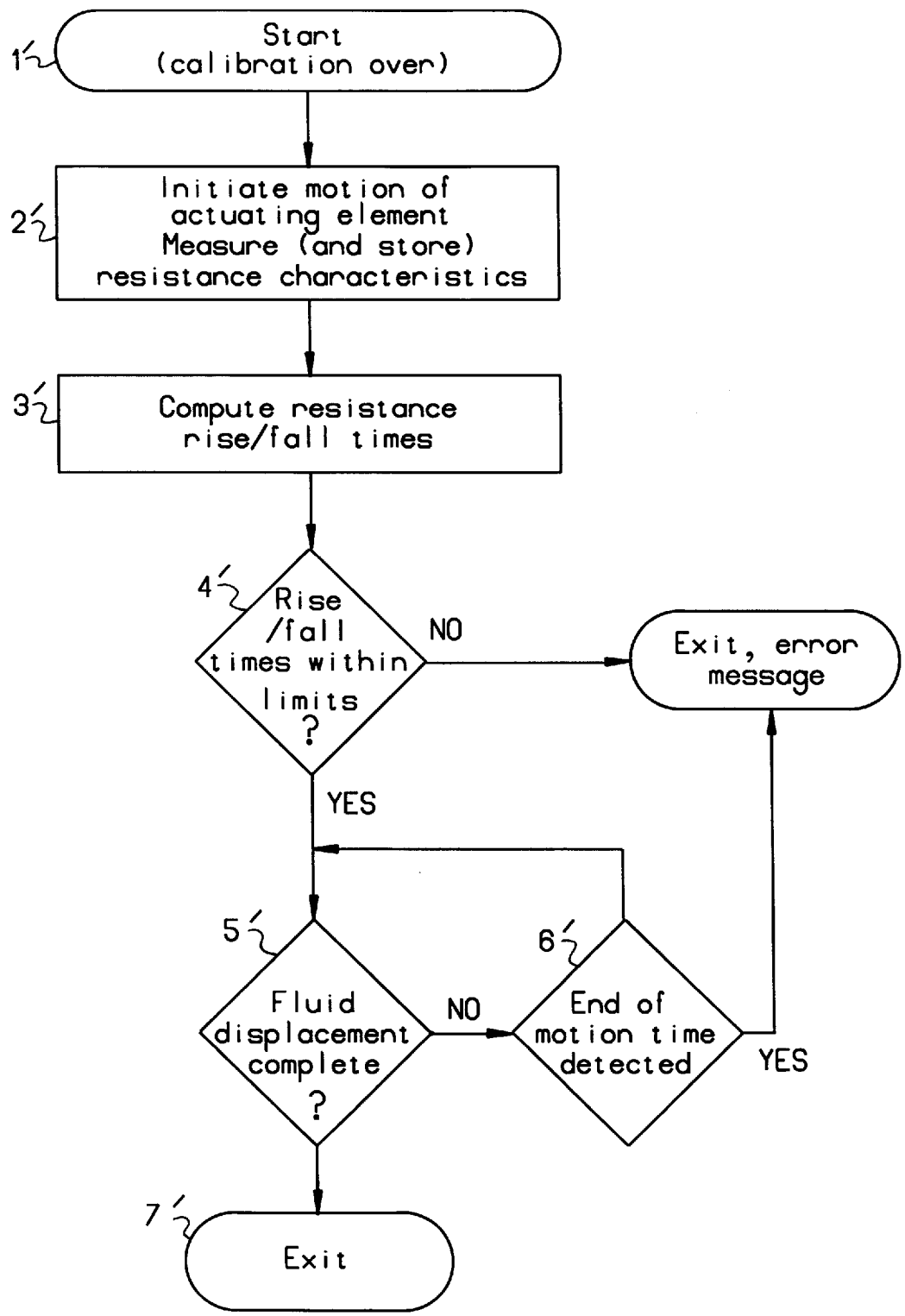
Figure 9B:
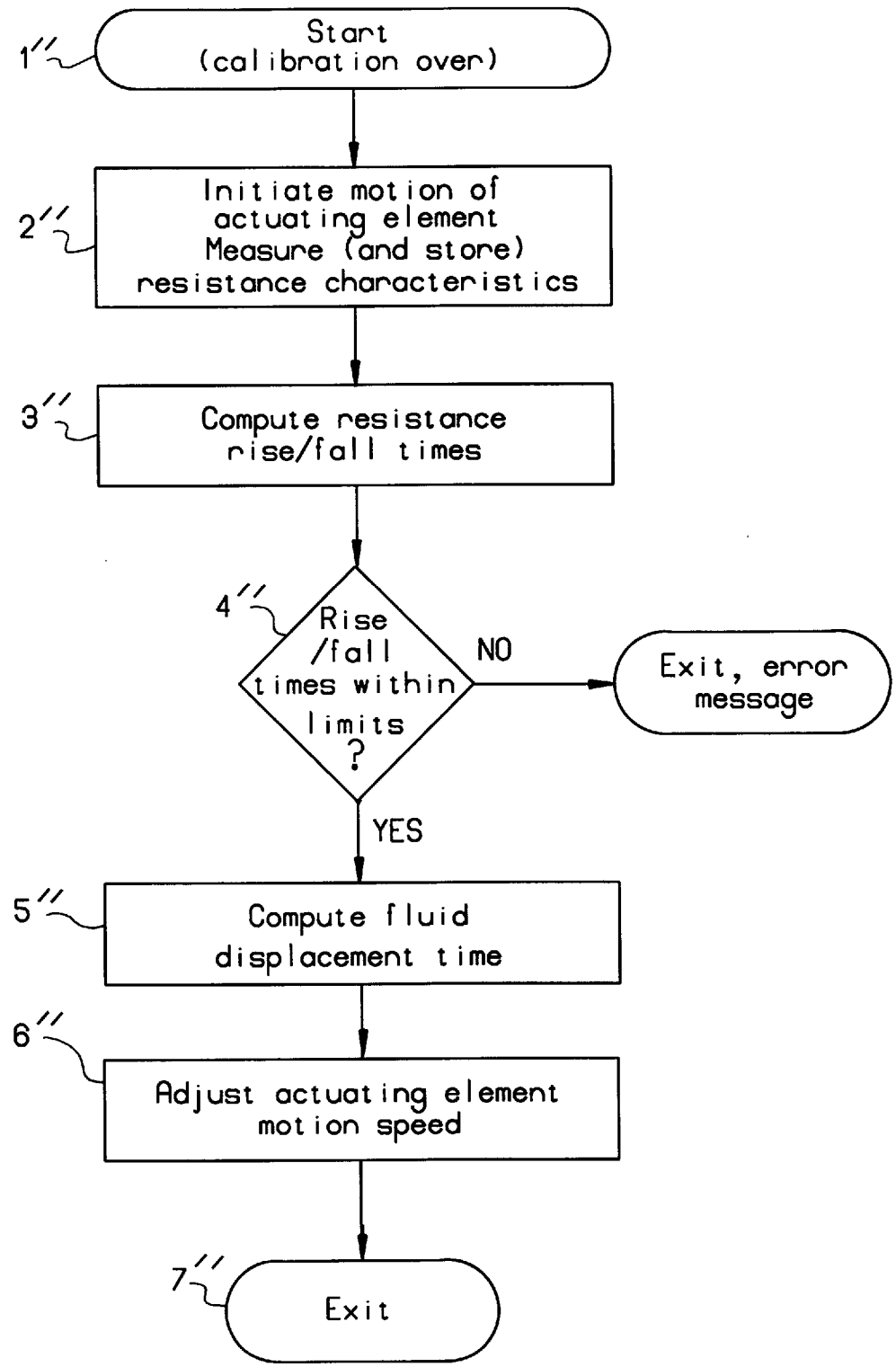

FIGS. 9A and 9B are block diagrams of a second and third preferred embodiments of the automatic compensation method of the present invention.

Figure 10:
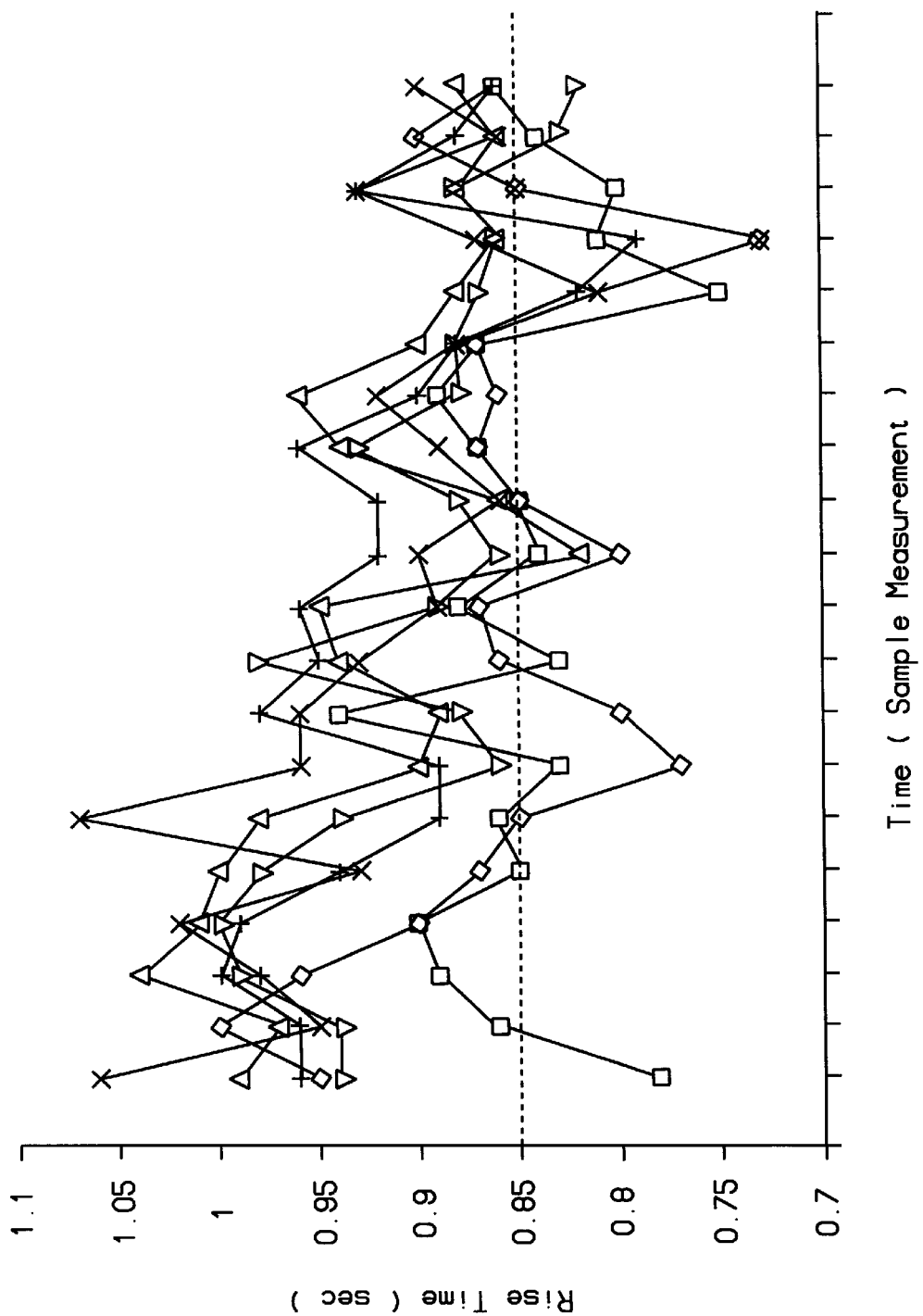

FIG. 10 is an illustration of effectiveness of the compensation method at moving the average air segment rise time to a target value.

DETAILED DESCRIPTION OF THE PREFERRED EMBODIMENTS

Figure 1:
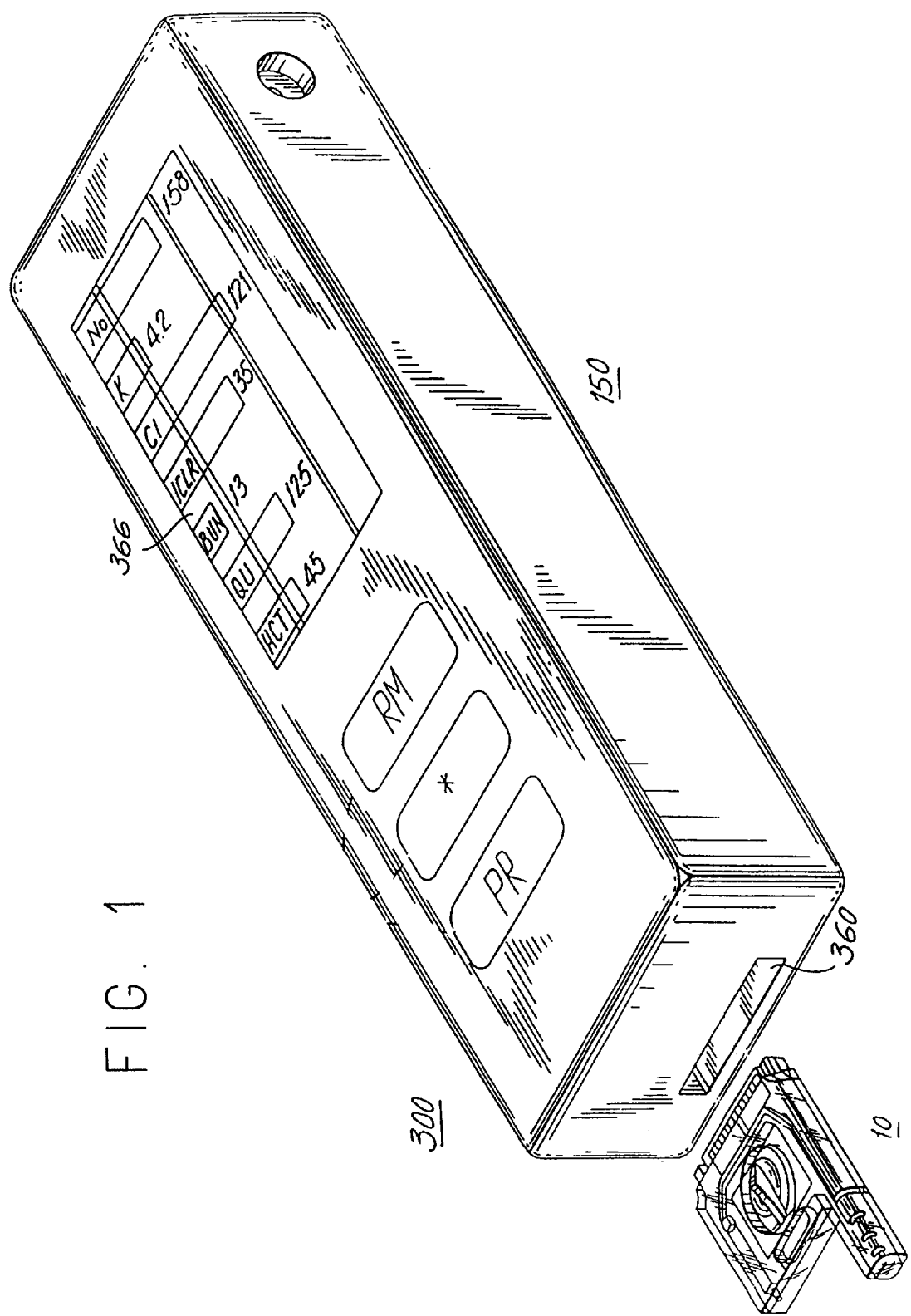
FIG. 1 is an isometric view of a reader instrument and a disposable cartridge used in the fluid analysis sensing device of the present invention.

Referring first to FIG. 1, the test system 300 of the present invention comprises a self-contained disposable sensing device 10 and a reader 150. To conduct the measurement, the test fluid sample to be sensed is first drawn into a chamber within the sensing device 10 which is then inserted into the reader 150 through slotted opening 360. Measurement results providing indication of the desired fluid sample concentrations are output to display 366 or other output devices, such as a printer. Following the test measurement, disposable sensing device 10 is automatically ejected and the reader instrument is prepared to receive the next sensing device.

Figure 2:
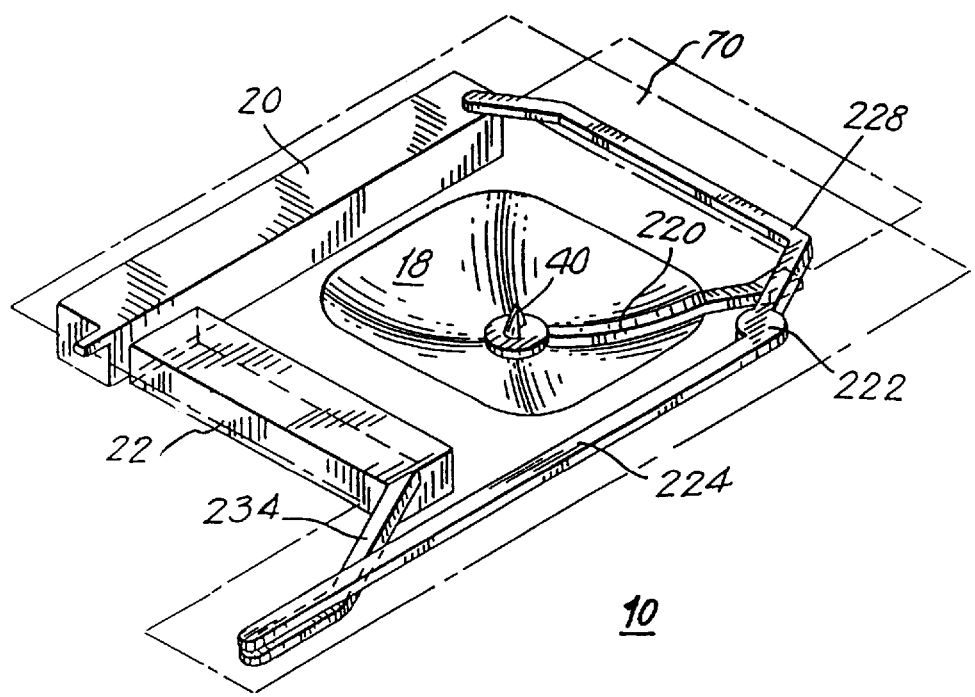
FIG. 2 is an isometric view of the disposable cartridge with its top portion removed.

Referring now to FIG. 2, sensing device 10 contains an array of sensor elements 70 and several cavities 18, 20, 22 and conduits 220, 224, 228, and 234 which enable the test fluid sample collection, provide active reagents, calibrate the sensors and enable the measurement by transporting fluids to and from the sensor elements 70.

Figure 4:
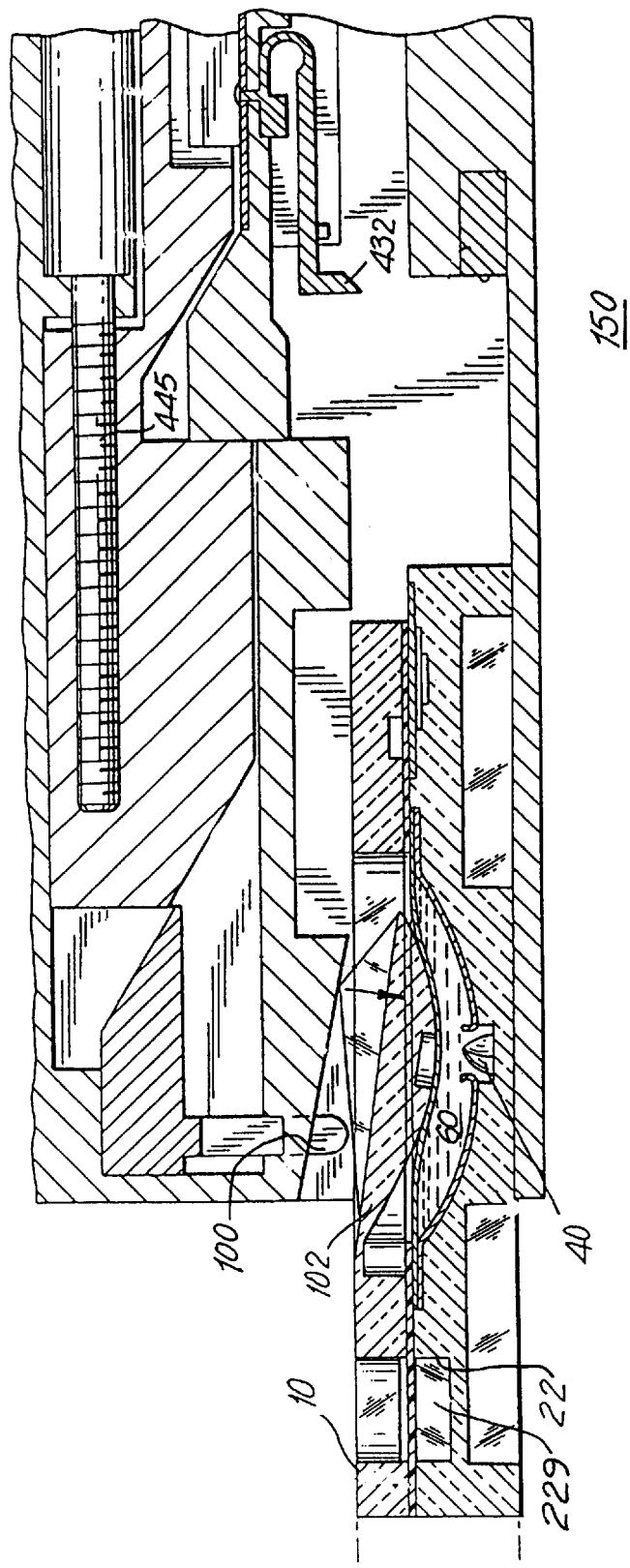
FIG. 4 is a cross-sectional view of the reader instrument with the disposable sensing cartridge partially inserted.

As shown in FIGS. 2 and 4 in the center of the device 10 is located first cavity 18 which has a pin 40 at its bottom, a hinged disk 102 at the top and a first conduit 220 which leads from cavity 18. A sealed pouch 60 containing fluid adapted to calibrate the sensor elements 70 resides in the cavity 18. A second conduit 224 has an orifice at one end for the receipt of a test fluid sample, while the other end terminates at a capillary break 222. A third conduit 228 leads from the capillary break 222 past the sensor elements 70 to a second cavity 20 which serves as a sink. The first conduit enters the third conduit between the capillary break and the sensor array. A third cavity 22 serves as an air bladder 229. When the air bladder 229 is depressed, air is forced down a fourth conduit 234 into the second conduit 224 displacing in the process the fluids within the sensing device.

Figure 3A:
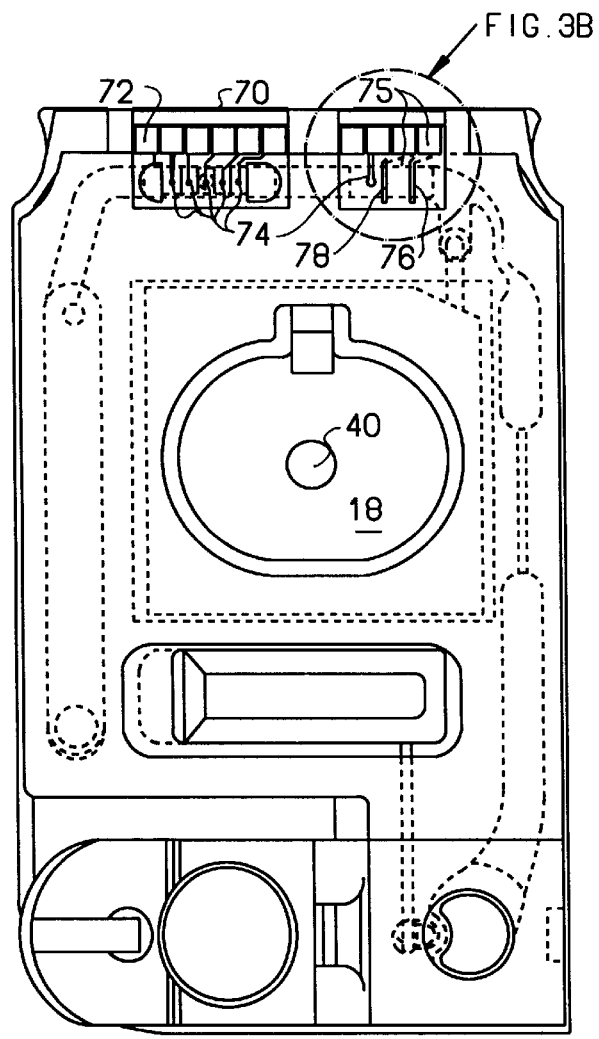
FIG. 3A shows in a diagrammatic form the fluid paths and the sensor elements shown in FIG. 2.

With reference to FIGS. 2 and 3A, the array of sensing elements 70 is designed to measure the specific chemical species in the fluid sample being tested. Preferably, each of the sensing elements comprises an array of conventional electrical contacts 72 and array of select chemical sensors 74 and circuitry for connecting individual sensors to individual contacts. The electrochemical sensors 74 are exposed to and react with the fluid sample to be measured generating electrical signals indicative of the measurements being performed. The electrical signals are output on the electrical contacts 72 which connect to an electrical connector of the reader 150 for the transmission of electrical potential values. A more specific description of the sensor array 70 is given in the incorporated '669 patent.

Figure 3B:
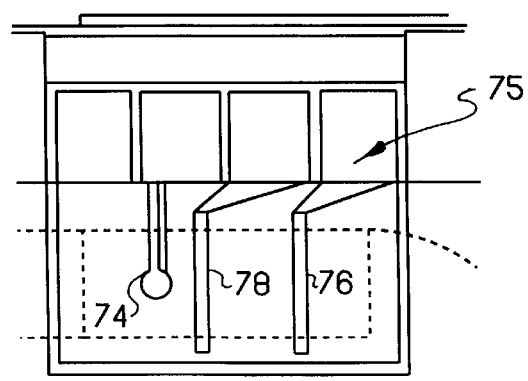
FIG. 3B is an exploded view of a portion of the diagram in FIG. 3A illustrating the conductivity sensors used in the compensation method.

FIG. 3A illustrates in a diagrammatic view the disposable sensing element of FIG. 2 in which like elements are denoted with like numbers. (The diagram includes a sealing cap portion not shown in FIGS. 1 and 2.) Particularly important for the present invention is sensor 75 which comprises a pair of conductivity electrodes 76 and 78 and is shown in an exploded view in FIG. 3B. Electrodes 76 and 78 are adapted to measure the electrical resistance of the substance between them, and communicate its value to the reader instrument.

In operation, when an orifice at one end of the conduit 224 is placed in contact with the test sample the fluid is first drawn by capillary action into the second conduit 224. After the test fluid sample fills the second conduit 224, the operator seals the orifice so that air from bladder 229 may force the fluid sample out of conduit 224.

In reference to FIG. 4, a cross section of the reader instrument 150 and the disposable device 10 is illustrated in a partially inserted form. When device 10 is fully inserted, electrochemical sensors 70 and conductivity sensor 75 come in contact with the electrical contacts 432 of the reader instrument indicating that the disposable sensing device is in position to start the measurement. At this time, pouch 60 is pierced causing the calibrant fluid to flow out of the pouch 60 through the first conduit 220 into the third conduit 228 and across the electrochemical sensing elements 70, where measurements are taken within a pre-specified time period (typically about 60 sec) to calibrate the sensing array.

In reference to FIGS. 2, 3, and 4, once the calibration is complete, a mechanical motor actuates the rotor 445 which moves in the direction toward the sensing device 10. An actuating element 100 is caused to press down at the air bladder 229 formed by cavity 22 and forces the air down the fourth conduit 234 into the second conduit 224 which in turn expels the test fluid sample from the storage conduit 224. The air forces the test fluid sample across the capillary break 222 and into the third conduit 228. The fluid sample is passed over the electrochemical sensing arrays 70 and forces the calibrant fluid in the conduit 228 to overflow into the waste sink defined by cavity 20. At this time, measurements are taken of the test sample which is in contact with the electrochemical sensors 70. The resulting electrical potentials, indicative of the concentration of the chemical species, are output on the electrical contact 72. These signals are transmitted through electrical connectors to the reader instrument which then performs calculations in accordance with a signal processing algorithm stored in a memory to determine the concentration of the measured species. This information is finally output to the display device or printer for use by the physician to perform medical analysis or diagnosis. Specifics of the operation of the device are disclosed in detail in U.S. Pat. No. 5,096,669 which is incorporated by reference.

FIGS. 5A, 5B, and 5C illustrate consecutive periods of the described fluid displacement cycle, where in FIG. 5A the fluid displacement has just begun (at time t0, immediately following the calibration of the sensor elements). FIG. 5B illustrates the second stage, when the calibrant fluid is being forced into the sink, and the air bubble separating it from the test fluid sample is positioned over the conductivity sensor. Finally, FIG. 5C illustrates the test fluid sample passing over electrodes 76 and 78.

It is important to note that the relative motion of the actuating element 100 of the sensing instrument is proportional to the number of revolutions made by a motor which drives the mechanically moving parts inside the reader 150. The number of revolutions can in turn be determined by monitoring the electromotive voltage generated by the rotor as it turns, this signal being proportional to the rotational speed. The number of turns of the rotor required to achieve certain vertical position of the actuating member 100 for a specific instrument can be programmed into a non-volatile memory chip in the factory. Specific mathematical relationships between the involved quantities are illustrated in Appendix A.

FIG. 6 illustrates a typical signal observed at the output of the conductivity sensor 75 in the course of the fluid displacement. The initial time t0 indicates the resistance measurement at the beginning of the fluid displacement, immediately following the calibration of the sensor arrays 70. In a preferred embodiment of the present invention the final time Te has a factory preset value which is determined in a compromise between the measurement. speed and the accuracy requirements, as discussed in U.S. Pat. No. 5,112,455 which is incorporated by reference.

Three well defined time segments are distinguishable in FIG. 6. The first segment, designated A, corresponds to the time period when the calibration fluid is being pushed out of the sensor area but is still determined by the resistance measured across electrodes 76 and 78 of sensor 75. This resistance has a typically low, constant value for a quiescent calibrant fluid. In the following time segment B, the air bubble separating the calibrant fluid and the test fluid sample is forced to pass over the sensors, drying their active areas. The air between the electrodes 76, 78 causes the measured resistance to increase significantly. (See time segment B in FIG. 6.) In the final time segment, denoted as C, the test fluid sample is forced by the motion of the actuating element to flow over the electrodes 76, 78. The typical test fluid samples are whole blood, which due to the concentration of electrolytes and non-conductive blood cells will have a resistance somewhat larger than that of the calibrant fluid but still much lower than the high resistance of the air bubble. As the test fluid sample flows over both sensors, flushing out any remaining calibrant fluid, the measured resistance settles to a constant value which corresponds to the electrochemical properties of the tested fluid sample. As is well known in the art, the individual time segments of the measurement may be separated by providing a threshold value(s), the crossing of which determines the boundaries between adjacent segments. (Thus, the time at which the measured resistance crosses a first resistance threshold TH1 defines the rise time t1 of the fluid displacement. Similarly, the time when the resistance drops below a second threshold value TH2 defines the fall time t2 of the fluid displacement).

The well defined time segments illustrated in FIG. 6 indicate the connection between the displacement of fluids during the test and the resistance signal from the conductivity sensors. This relationship is the basis for the automatic compensation method of the present invention.

FIGS. 7A, 7B, and 7C illustrate in a diagram form several possible resistance curves in which the time segments A, B and C deviate from the normal ones, due to mechanical wear, variations in the fill of fluids in the sensing device, variations in cartridge to cartridge parameters, the viscosity of the sample, and other factors. As indicated, the change in these figures, compared to the normal resistance curve defined in FIG. 6, is shown as an increase or decrease in the rise time t1 and a shift of the fall time t2 of the resistance curve, correspondingly. It is clear that time segment C which corresponds to the time during which the test fluid sample is being brought across the conductivity sensor varies. As the fluid tested by the other sensors is a mixture of the calibrant and test sample fluids, due to a small amount of "carryover," the variation in the amount of sample brought to the sensors leads to a component of variation of the measurements made by all the sensors in the sensing device 10.

The deviations from the normal resistance curve, illustrated in FIG. 7 indicate imprecisions in the amount of test sample passing over the sensors, the volume of the separating air segment and thus the amount of calibrant fluid which is carried over into the sample which is measured by the sensors. Most of these variations are random from cartridge to cartridge and are caused by variations in the physical dimensions and characteristics of the different cartridges, the amount of test sample fluid, and the sample fluid viscosity. Additionally, there is a component of these variations that slowly increases over the life of the instrument as the mechanical parts wear. This wear typically causes a shift in the initial position of the actuating element 100, which shift increases with the number of samples being tested.

The goal of the automatic compensation method of the present invention is to counteract the factors which may contribute to the deviations of the test conditions from sample to sample. In accordance with a preferred embodiment of the invention, this is accomplished by delivering a constant volume of test sample to the sensors at a constant speed. This volume is determined by both the initial position of the actuating element of the reader 150 at the end of the calibration period, and the length of the fluid displacement period. By monitoring the electrical resistance response curve from the fluid displacement, it is possible to evaluate the performance of the mechanical fluid control system after each test and compensate for minor variations from the factory preset standard (target) values.

FIG. 8 is a block diagram of the method for automatic compensation in accordance with a preferred embodiment of the present invention. At step 1 actuating element 100 is positioned just above the air bladder 229 at the end of the calibration period and the actual fluid displacement is ready to start (t=t0). Calibrant fluid is still covering the electrodes 76, 78 of sensor 75 and the measured resistance between them is low.

At step 2, the fluid displacement is initiated as actuating element 100 is moved downward for a preset period of time, typically 3.5 seconds. The motion of element 100 causes air in air bladder 229 to displace all fluids within the fluid paths of the sensing device 10, as described above. At the same time, measurements of the resistance curve from conductivity sensor 75 can be stored in a digitized form into a RAM memory within the reader.

At step 3, the resistance rise and fall times t1 and t2, as defined in FIG. 6, are computed by comparing factory preset values stored in a non-volatile memory within the reader 150 to the resistance measurement from sensor 75.

In the next step, step 4 in FIG. 8, the computed rise time t1 is compared to factory preset limits. Should the measured value exceed those limits, an error message is displayed and the test is discontinued. This computation step is designed to uncover gross deviations from the normal test parameters, such as a defective sensing device, lack or insufficient test fluid and others. By discarding such deviating samples, the method of the present invention avoids the use of abnormal test characteristics in the compensation feedback loop. The limits may be determined statistically after examining a number of test samples known to be good.

If the processing measurements are within limits, in the following step 5 the test measurement proceeds to the end of the predetermined time period T. If the rise/fall times t1/t2 had not been previously stored at step 2, they are now stored in a RAM memory of the sensing instrument.

In step 6 of the method, the recorded rise time t1 of the resistance measurement is compared to a factory pre-specified threshold value (typically for blood tests this threshold is set at 0.85 seconds) which corresponds to the average expected resistance rise time. The sign of the computed difference at step 6 determines the direction of the motion compensation in step 7 of the method. For example, if the rise time t1 is shorter than the factory preset value, the compensation method automatically adjusts the initial position of the actuating element 100 to start the actual fluid motion somewhat later during the next fluid displacement operation. If the measured rise time is longer than the preset factory value, the method compensates by adjusting the initial position of the actuating element so that for the next test cartridge the fluid motion will start earlier. Alternatively, it may be the resistance fall time t2 which is compared to a factory pre-set target value and used to determine the corrections in the position of the actuating element.

In accordance with the present invention, the correction value is stored as bits in a RAM memory within the reader 150. To reduce the sensitivity of the method to normal sensing device-to-device deviations around the mean test conditions, which deviations may still fall between the limits at step 4, after each test measurement the amplitude of the correction to the actuation element motion is preferably kept constant. However, other correction algorithms within the spirit of the inventive concept may also be employed if required. The initial position of the actuating element at the start of the next fluid displacement is determined by two factors: a factory preset value which is typically stored in a non-volatile memory of the reader; and a compensation value, which depends on the sign of the rise time comparisons for the previous test samples and is accumulated in a RAM or an EEPROM memory of the reader 150. Thus, if the parameters of the test measurements are consistent over a number of samples, the compensation value will be close to zero, so that the position correction of the actuating element from test to test will alternate between positive and negative. Alternatively, if the rise time for a group of sensing devices is consistently larger or smaller than the factory preset value, the corresponding correction accumulates, causing with each test the position of the actuating element to compensate for the changes until the instrument adaptively brings the test conditions to the standard.

Using conversion tables such as those shown in Appendix A, at step 8 of the method the stored corrections are translated into a physical motion of the actuating element (the correction is in fact stored as the number of revolutions of the actuating motor). This motion determines the position of the actuating element at the beginning of the next fluid displacement. Once this motion is determined, the compensation algorithm exits (step 9), leaving the device ready for the next test sample.

It should be noticed, that in order to minimize the memory accesses to non-volatile memories which may have a limited number of read/write cycles, the compensation algorithm of the present invention may be adjusted to make a correction of the actuating element's motion every M-th step, instead of using a correction after each measurement (M typically ranging from 2 to 100).

FIGS. 9A and 9B are block diagrams of a second and third embodiment of the present invention. These method embodiments are based on the fact that the speed of the actuating element and the time for completing the measurement of the test sample may be accurately controlled by appropriately programming the motion of the actuating element.

In accordance with the second embodiment of the present invention, a target time for a standard test fluid sample to pass over the sensors is used. (time segment C in FIG. 6). For a constant speed of the actuation element this time is proportional to the sample volume moved over the sensor elements, so that by keeping the time during which the sample fluid is passing over the sensors constant, the compensation method of the present invention effectively maintains a constant test sample volume.

Steps 1' and 2' of the method are similar to those in FIG. 8 but the instrument continuously monitors the output of the conductivity sensors. After the measured resistance reaches the second predetermined threshold TH2 (at the falling time of the resistance curve), at step 3' of the method, the computed resistance rise/fall times are compared at step 4' to threshold limits causing the algorithm to exit, should abnormal deviations be detected. At step 5', the actuation element 100 is continuously pressed for the predetermined average test time at step 6', if prior to the test completion there is indication of the end position of the actuating element, the compensation algorithm exits with an error message. Otherwise, the test ends at step 7' indicating a normal test sample measurement. In this embodiment, the motion speed of the actuation element is kept constant for each test measurement.

In a third preferred embodiment of the present invention, a target volume of the test sample is passed over the sensors for each test measurement by keeping the fluid actuation time constant but modifying the speed of the actuating element. FIG. 9B shows a detail of the compensation method in accordance with this embodiment, where like algorithm steps are denoted with like numbers. The method steps 1"–4" are similar to those in FIG. 9A. At step 5", after the resistance fall time t2 is determined, the algorithm computes the time for a standard test fluid sample to pass over the sensors (segment C in FIG. 6) for the particular test measurement by subtracting the fall time from the predetermined overall test time. In step 6" the computed test fluid sample time is used to calculate the speed of the actuating element which is required in order to displace the target sample fluid volume. The speed adjustment is done in real time, so that at step 7" the algorithm exits at the end of the test measurement.

In all embodiments of the present invention, the automatic compensation methods are implemented by storing into the memory of the reader instrument the corresponding algorithm steps and executing the routines during or after the actual test measurement. One or more algorithms which correspond to the above described embodiments may be stored and used at different times according to needs. The proposed compensation methods do not require hardware modifications of the device disclosed in the '669 patent, however, they contribute to reducing variations of test measurement parameters. The software based automatic compensation effectively increases the consistency and reliability of the output measurements of the i-STAT fluid sensing system.

FIG. 10 is an illustration of the typical sensing device to device variations and the results of the compensation method in accordance with the first preferred embodiment of the present invention. Each line represents a series of rise time measured by individual instruments. The compensation method of the present invention is seen to move the average rise time toward the target value of 0.85 seconds. The initial deviation from the target value may be due to mechanical wear or misadjustment caused by mishandling or other factors. While the automatic compensation method moves the average time toward the target value, it does not remove the inherent sensing device to device variability. This inherent variability contributes one component to the variability of the measurements made by the sensors. The compensation method of this invention reduces the contribution of other error components which gradually affect the performance of the sensing instrument as it is being used.

While the present invention is particularly advantageous in the medical environment and has been described in this context, it will be appreciated that it can be practiced in any situation where it is desired to perform chemical analyses of a large number of test fluid samples and is required to keep the test parameters relatively unchanged. In addition, it is to be expressly understood that the claimed invention is not to be limited to the description of the preferred embodiments but encompasses other modifications and alterations within the spirit of the inventive concept which scope is defined by the following claims.

APPENDIX A

Physical Constants in the Sensor Instrument

1. Relating Change in Actuating Element Position to Change in Air Segment Time.
2. Relating Change in Actuating Element Motion to Back-EMF Bits J = Y/R    [mils/rotation]
   G = r/R    [dimentionless]
   k = V/W    [mVolts/1000's rpm]
   E          [mV*mS/bit]
   (E signifies that 1 bit corresponds to a unit back-EMF for a unit period of time)
   where the quantities above are defines as follows:

| | | |
   |---|---|---|
   | Actuating element Motion | Y | [mils] |
   | Rotations of Leadscrew | R | [rotations] |
   | Rotations of Motor | r | [rotations] |
   | Rotation Rate of Motor | W | [rotations per msec] |
   | Back-EMF Voltage | V | [millivolts] |
   | Integrated Back-EMF | B | [bits] |
   | Time | t | [msec] |

Dimensional Constants:
   1000 rotations per minute = (1/60) rotations per millisecond
   so to express k in consistent dimensions use
   60*k mV/rotations per msec
   Using the above definitions, the ratio B/Y can be derived as:

$$B/Y = (60*k*G)/(J*E)$$

which is the expression used to control the motion of the actuating element.

What is claimed is:

1. An automatic compensation method for maintaining close to a target value a mean fluid displacement of test samples in a succession of test measurements of a fluid sensing instrument which includes an actuation mechanism for the displacement of at least one fluid along a predetermined fluid path and at least one sensor, the method comprising the steps of:

(a) recording the time of arrival of each fluid at the sensor by measuring an output characteristic of the sensor;
   (b) for each successive test measurement determining the variation of the recorded arrival time from a predetermined value; and
   (c) compensating, in response to the determined variation, the motion of the fluid actuation mechanism in successive test measurements to keep the mean fluid displacement close to the target value.

2. The method of claim 1 wherein the fluid path and the sensor are positioned in a disposable cartridge device replaced after each test measurement.

3. The method of claim 1 wherein measurements of the output characteristics of the sensor in step (a) are stored in a memory during each test measurement and are compared at step (b) of the method to a value determined by a factory preset value corresponding to an average expected fluid arrival time.

4. The method of claim 1 wherein step (b) further comprises the step of comparing the determined variation to preset maximum deviation limits and discontinuing the test measurement if the determined variation is larger than the preset limits.

5. The method of claim 4 wherein the motion compensation of the actuation mechanism at step (c) is computed for each test sample from a factory preset value corresponding to an average expected fluid arrival time for test samples and from a value which is determined by the cumulative correction of variations in the previous test measurements.

6. The method of claim 4 wherein a unit compensation of the motion of the fluid actuation mechanism at step (c) in each test measurement has a constant value which is independent of the value of the determined variations which are within the maximum deviation limits.

7. The method of claim 1 wherein a unit compensation of the motion of the fluid actuation mechanism at step (c) in each test measurement is done in response to the sign of the determined variation.

8. The method of claim 1 wherein the sensor measures the electrical conductivity of the fluids passing along the fluid path.

9. The method of claim 8 wherein fluid samples in one test measurement having similar electrical conductivities are physically separated as to cause large deviations in the measured electrical conductivity signal at the output of the sensor.

10. The method of claim 1 wherein in step (c) the compensation is different from a zero value only for every M-th measurement, where the value of M is selected between 2 and 100.

11. The method of claim 2 wherein the compensation of the fluid actuation mechanism is adapted to reduce the effects of a physical wear of the parts of the sensing instrument over a number of test measurements.

12. The method of claim 2 wherein the compensation of the fluid actuation mechanism is adapted to reduce the effects of the differences between individual fluid test samples over a number of test measurements.

13. The method of claim 1 wherein the test measurement for each test sample is conducted in a prespecified constant time.

14. A system for sensing at least one component concentration in a fluid test sample, comprising a reading apparatus and a disposable sensing device, the disposable sensing device comprising:

at least one sensor;
   sample retaining means for retaining the fluid sample out of contact with the sensor prior to sensing;
   a sample conduit connecting the sample retaining means with the sensor; and
   sample displacement means for automatically and forcibly displacing the sample through the sample conduit and into contact with the sensor to enable sensing; the reading apparatus comprising:
   receiving means for receiving the disposable sensing device;
   control means for controlling the automatic displacement of the fluid test sample by the sample displacement means of the disposable sensing device;
   first memory means to store output characteristics of the sensor; and
   automatic compensation means for maintaining close to a target value the mean fluid displacement by adjusting input parameters of the control means in response to the stored output characteristics following each measurement.

15. The system of claim 14 wherein the reading apparatus further comprises a second memory means to store preset values and means for comparing values stored in the first memory means and the second memory means to determine input parameters of the compensation means.

16. The system of claim 15 wherein the reading apparatus further comprises means for displaying the results of the sensing and for providing an indication to the user whenever the output characteristics of the sensor are outside specified limits stored in the second memory means.

17. The system of claim 14 wherein said target value of the mean fluid displacement is dynamically adjustable.

18. An automatic compensation method for maintaining close to a target value the mean fluid displacement samples in a succession of test measurements of a fluid sensing instrument which includes an actuation mechanism for the displacement of fluids along a predetermined fluid path during each test measurement and at least one sensor, the method comprising the steps of:

(a) storing in memory means a parameter associated with the target value of test fluid volume required to pass over the sensor;

(b) recording the time of arrival of the test fluids at the sensor by measuring an output characteristic of the sensor;

(c) following the recorded time of arrival, for each test fluid sample comparing an output characteristic of the sensor to the stored parameter value; and (d) compensating in response to the comparison the motion of the fluid actuation mechanism to keep the mean test sample fluid volume close to the target value.

19. The method of claim 18 wherein the parameter associated with the target value of test fluid volume is the time required for the test sample to pass over the sensor for a constant speed of motion of the fluid actuation mechanism.

20. The method of claim 18 wherein the parameter associated with the target value of test fluid volume is the speed of motion of the actuation mechanism for a constant test measurement time.

* * * * *